United States Patent [19]
Gross

[11] Patent Number: 5,871,125
[45] Date of Patent: Feb. 16, 1999

[54] CHEMICALLY DRIVEN LIQUID DELIVERY PUMPING DEVICE

[75] Inventor: Joseph Gross, Dublin, Ireland

[73] Assignee: Elan Medical Technologies Limited, Athlone, Ireland

[21] Appl. No.: 697,692

[22] Filed: Sep. 5, 1996

[30] Foreign Application Priority Data

Sep. 5, 1995 [IE] Ireland ..................................... 950680
Jan. 2, 1996 [IE] Ireland ..................................... 960001

[51] Int. Cl.$^6$ ................................................... B65D 83/14
[52] U.S. Cl. .......................... 222/207; 222/214; 222/389; 222/397; 222/399; 604/145; 604/147
[58] Field of Search .................... 222/207, 214, 222/389, 399; 604/82, 83, 131, 141, 142, 145, 147, 896, 407, 416

[56] References Cited

U.S. PATENT DOCUMENTS

| 3,235,135 | 2/1966 | Robert et al. | 222/207 |
| 4,140,117 | 2/1979 | Buckles et al. | 128/213 |
| 4,886,499 | 12/1989 | Cirelli et al. | 604/131 |
| 5,090,963 | 2/1992 | Gross et al. | 604/132 |
| 5,163,909 | 11/1992 | Stewart | 604/140 |
| 5,398,850 | 3/1995 | Sancoff et al. | 222/386.5 |
| 5,398,851 | 3/1995 | Sancoff et al. | 222/386.5 |

FOREIGN PATENT DOCUMENTS 0 494 042 A2  7/1992  European Pat. Off. ....... A61M 5/155
950366  1/1998  Ireland .

Primary Examiner—Andres Kashnikow
Assistant Examiner—David Deal
Attorney, Agent, or Firm—Kathleen L. Maher

[57] ABSTRACT

A liquid delivery pumping device for the delivery of liquids enterally or parenterally comprises a housing including a gas generating chamber, wherein a gas is generated intermittently when two reactants, such as the components of an effervescent couple, are caused to react, a pumping chamber for a reciprocating pumping unit operable by the gas and to which chamber the gas is conveyed once generated, the pumping unit forming part of a mechanism which receives and regulates the liquid to be delivered in response to the reciprocation of the pumping unit, and means for controlling the gas pressure within the pumping chamber to enable controlled reciprocation of the pumping unit. The device provides precisely controlled rates of liquid delivery to a patient irrespective of the viscosity of the liquid to be delivered.

26 Claims, 10 Drawing Sheets

CHEMICALLY DRIVEN LIQUID DELIVERY PUMPING DEVICE

FIELD OF THE INVENTION

This invention relates to liquid delivery devices for the controlled delivery of a liquid to a patient of the type employing gas generation as a means of assisting the delivery of said liquid.

BACKGROUND OF THE INVENTION

There are many examples of drug delivery systems which operate using gas pressure to deliver a liquid such as a nutritive liquid at a controlled rate. U.S. Pat. No. 5,398,851 discloses a device comprising a casing having a liquid-tight membrane disposed therein which divides the interior of the casing into a propellant chamber and a liquid chamber or reservoir for the liquid to be delivered. The reservoir is in communication with an outlet. The propellant chamber contains two chemicals such as sodium bicarbonate and citric acid which are initially separated from one another by a barrier. Delivery is effected by breaking or perforating the barrier to allow the acid and bicarbonate to come into contact and thereby generate carbon dioxide gas. The carbon dioxide expands the propellant chamber by pushing on the membrane, thereby contracting the reservoir and causing liquid to be delivered from the casing via the outlet port.

Patent application Ser. No. 950366 discloses a feedback-controlled liquid delivery device which generates gas only as it is needed and therefore has advantages over the device of U.S. Pat. No. 5,398,851 due to the fact that it can maintain gas generation for a relatively long period of time (the device of U.S. Pat. No. 5,398,851 has a gas generator which, when actuated, proceeds until it is exhausted, even if delivery is stopped).

However, the devices of both U.S. Pat No. 5,398,851 and patent application Ser. No. 950366 each maintain a predetermined pressure within the system to drive the liquid from a reservoir, within the device, to a patient.

Neither the device disclosed in U.S. Pat. No. 5,398,851 nor the device disclosed in patent application Ser. No. 950366 can guarantee a predictable pumping rate under all conditions. This is because the viscosity of a liquid to be delivered must be considered when dealing with delivery devices containing an outlet of fixed size. If the liquid reservoir is pressurised to a predetermined pressure and the liquid is forced through an outlet of a fixed size, then it is the viscosity of the liquid which determines the rate of delivery through said outlet. The viscosity of a liquid can vary due to the influence of outside parameters such as temperature, and problems can arise during manufacture in producing a liquid of constant viscosity.

A further disadvantage associated with the device of U.S. Pat. No. 5,398,851 is that it requires a reservoir which can withstand the driving pressure of the generated gas and this eliminates the use of conventional bottles or bags which are not adapted to withstand elevated internal pressures.

SUMMARY OF THE INVENTION

The invention seeks to provide an improved liquid delivery device which will provide precisely controlled rates of liquid delivery to the patient irrespective of the viscosity of the liquid to be delivered and which can be used with conventional liquid supply containers.

Thus, the invention provides a liquid delivery device comprising a housing, a pumping chamber within the housing, gas generating means comprising reactants which when brought into contact generate a gas which pressurises said pumping chamber, a pumping mechanism having a pumping member within the pumping chamber, said member being reciprocable in response to changes in pumping chamber pressure, wherein the reciprocation of the pumping member causes a liquid to be drawn from a liquid supply and pumped towards an outlet, and means for controlling the pressure within the pumping chamber to enable controlled reciprocation of the pumping member.

As the device acts by drawing a liquid from a liquid supply and subsequently pumping it towards an outlet, rather than by pressurising a reservoir, the problems associated with the prior art are avoided. The device can therefore be used with any type of conventional liquid supply, in particular with conventional nutritive liquid supplies.

Furthermore, the device is powered by the generation of gas when two or more reactants are mixed together. This is an extremely cheap and powerful method of gas generation and is therefore advantageous when compared to electrolytic cell or expanding gels, for example.

Suitably, the means for controlling the pressure within the pumping chamber comprises a vent having associated control means.

Preferably, the vent is an electronically controlled valve unit which when actuated releases gas from said pumping chamber.

If the rate of generation of gas is precisely known, then the provision of a vent with associated control means, in particular an electronically controlled valve unit, allows for a very stable and controlled pressurisation/depressurization of the chamber and a correspondingly controlled reciprocation of the pumping member. This in turn leads to a highly controllable and predictable pumping and delivery rate.

Suitably, the vent comprises an electromagnetically actuated valve member for selectively causing a venting aperture in the housing to be blocked and unblocked.

This type of vent requires very little power as even a small movement of an electromagnetically actuated valve member is sufficient to unblock the aperture. Many prior art devices rely on automatic vents such as snap valves or slow acting vents, but an electromagnetically actuated valve member is again more controllable and predictable in operation than an automatic mechanical vent or valve.

Preferably, the pumping mechanism comprises valve means for causing liquid to be drawn from the liquid supply into the pumping mechanism and subsequently pumped from the pumping mechanism towards the outlet upon the reciprocation of the pumping member through a cycle.

This type of valve converts the reciprocating action of the pumping member into a unidirectional flow of the liquid to be pumped. The valve means can comprise two or more valve members or can comprise a single member as described below.

Preferably, the pumping member is in the form of a convoluted diaphragm.

According to a preferred embodiment, the diaphragm is in the form of a bellows.

The advantage of using a bellows or a similarly convoluted pumping member is that it can be reciprocated by expanding and contracting its internal volume between known limits thereby giving rise to a constant pumping volume on each cycle of reciprocation.

Suitably, the bellows has inner and outer walls defining a channel therebetween through which gas can escape to the atmosphere if the outer wall of the bellows is perforated.

This feature provides additional safety and prevents the gas which is being generated within the device from being transmitted to the patient in the event that the bellows (or, indeed, any other pumping member) becomes perforated or detached.

Preferably, the bellows comprises an elastic member which when relaxed causes the bellows to be extended but which can be elastically deformed allowing the bellows to be compressed under an increased chamber pressure.

The elastic member may be attached to the bellows externally or internally or the elasticity may be integral to the construction of the bellows. The degree of elasticity is chosen according to the volume, rate and nature of the liquid being pumped and the rate at which gas is being generated.

Suitably, liquid is drawn into the bellows and pumped therefrom during a cycle of reciprocation of the bellows, such that the volume of liquid which is pumped during each cycle of reciprocation is equal to the difference between the extended and compressed bellows volumes.

Further, suitably, the means for controlling the pressure causes the pumping chamber pressure to vary cyclically, the cycle comprising a compression phase during which the pumping chamber is pressurised by the generation of gas to a sufficient pressure and for a sufficient time to cause the bellows to be compressed to a predetermined extent, and a relaxation phase during which the pumping chamber is depressurized by a sufficient amount and for a sufficient length of time to allow the bellows to re-extend to a predetermined degree and thereby draw in a fixed volume of liquid to be pumped during the following cycle.

This cycle of reciprocation gives rise to a pumping cycle which is constant and independent of viscosity. It will be appreciated that if the viscosity of the liquid is somewhat less than expected, then the only effect is that the bellows will empty more quickly during the compression phase and refill more quickly during the relaxation phase. The point is, however, that the compression phase always lasts for a constant length of time and the relaxation phase always lasts for a constant length of time, and so the volume of liquid pumped during one complete cycle of reciprocation is always the same and is independent of viscosity. Similarly, if the viscosity increases for any reason, the emptying and refilling of the bellows will each take longer, but the compression phase and relaxation phase will be chosen to be sufficiently long to take account of these increases. Therefore while the bellows empties more slowly and refills more slowly, a full volume is pumped and the cycle nevertheless takes the same length of time, and, therefore, there is no difference in the overall pumping rate. With the prior art devices which are pressure dependent, the delivery rate would simply increase or decrease in accordance with a decrease or increase in viscosity.

According to one embodiment of the invention, the pumping member is a first bellows and the pumping mechanism includes a second bellows cooperating with the first bellows such that the first bellows is operated on by said gas to cause reciprocation of the second bellows.

Like the embodiment in which the bellows has inner and outer walls, this embodiment also separates the gas and the liquid by more than a single layer and provides an added safety feature.

Preferably, in this embodiment, the valve and the second bellows form a unit which is detachable from the device for reuse once the gas generating reactants are exhausted.

The unit comprising the valve and second diaphragm can be supplied separately from the remainder of the device. This arrangement may be commercially preferable.

Preferably, any gas escaping through the first diaphragm vents to the atmosphere.

Suitably, the gas generating means comprises first and second compartments, each containing a reactant, said compartments being interconnected in a manner which permits the flow, in use, of a reactant from the first compartment to contact the other reactant.

Alternatively, the reactants may be initially separated and subsequently brought into contact en masse to provide the gas generating reaction.

Preferably, the reactants are two reactants which consist of the components of an effervescent couple.

According to a preferred embodiment, the reactants are citric acid and either sodium bicarbonate or sodium carbonate and the gas generated is carbon dioxide.

These reactants are available very cheaply and are widely used in industry, and they are therefore very suitable for use in a gas generator of this type. In addition, the by-products of the gas generating reaction can be easily and safely disposed of.

Suitably, at least one rupturable seal separates said reactants prior to the reaction of and generation of gas thereby.

According to a preferred embodiment, the device further comprises a gas generation chamber in which said gas is generated and which is in communication with said pumping chamber.

The advantage of this arrangement is that it is possible to prevent gas from entering the pumping chamber while it is open to the atmosphere, thereby saving on wasting reactants, i.e. when gas is needlessly vented into the atmosphere.

Suitably, therefore, the device further comprises blocking means for preventing further ingress of gas into the pumping chamber while gas is being released therefrom.

Preferably, said blocking means is incorporated into said vent.

Most preferably, said blocking means comprises a blocking member which is controllably movable from a first position, in which it blocks a venting aperture between the pumping chamber and the atmosphere, to a second position in which it blocks communication between the gas generation chamber and the pumping chamber, such that the movement of the blocking member between the first and second positions enables the pumping chamber to be selectively pressurised and depressurized.

This enables a single mechanism to be used to simultaneously vent the pumping chamber to the atmosphere and prevent further gas from entering into the pumping chamber while it is open to the atmosphere.

Advantageously, the gas generating means enables a gas to be generated intermittently.

Preferably, an increase in pressure within the gas generation chamber prevents continued mixing of the reactants.

By blocking communication between the gas generation chamber and pumping chamber at the same time that the venting aperture is opened between the pumping chamber and the atmosphere, one not only achieves the advantages referred to above, but in addition, blocking communication in this way leads to an increased pressure within the gas generation chamber which can prevent continued mixing of the reactants. One thereby generates a gas intermittently, automatically tailoring the generation of gas to meet the pumping requirements. In other words, gas is only generated when it is needed. Furthermore, if, for any reason, the venting mechanism becomes blocked, generation will not continue indefinitely but will cut itself off when the pressure reaches a certain level, thereby providing another safety feature.

Preferably, one of said reactants is in liquid form and flows from a compartment into contact with the or each other of said reactants and wherein an increase in pressure within the gas generation chamber reduces the rate of flow of said one of said reactants.

If a reactant flows through a small aperture, then an increase in the gas pressure in the area into which the reactant is flowing can serve to cut off the flow of reactant. Similarly, one can have a blocking member which is acted upon by increasing gas pressure to block an aperture and thereby cut off the flow of reactant.

This arrangement allows the generation of gas to be stopped when it is not needed, thereby substantially reducing the amount of reactants needed to ensure operation of the device for a given period of time. In many prior art nutritive liquid delivery devices, and in some of the simpler embodiments of the present invention, two reactants are simply added together and the reaction proceeds at full speed until the reactants are exhausted. By generating a gas intermittently, however, one can economise greatly on the reactants, thereby making the device more efficient and also making the manufacture of the device more environmentally friendly by economising on natural resources.

BRIEF DESCRIPTION OF THE DRAWINGS

The invention will be further illustrated by following description of embodiments thereof, given by way of example only, with reference to the accompanying Drawings, in which.

DETAILED DESCRIPTION OF THE INVENTION

Figure 1:
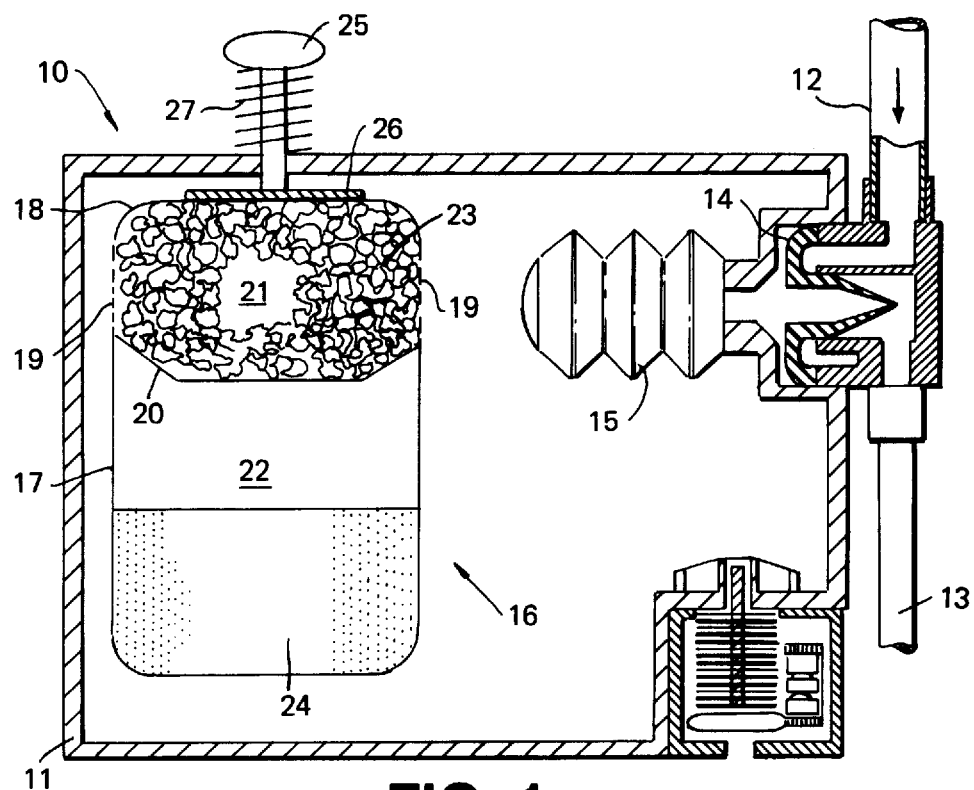
FIG. 1 is an end elevation in section of a liquid delivery device according to the invention, before use.

Referring to FIG. 1 of the drawings there is indicated, generally at 10, a liquid delivery device according to the invention. Device 10 comprises a housing 11 which receives a supply tube 12, which leads for example from a conventional nutritive liquid supply bottle or drip bag (not shown), and a delivery tube 13 which leads to a patient. A nutritive liquid can therefore pass from the nutritive liquid supply to the patient via an inlet/outlet valve 14 which permits communication between the tubes 12,13 via a reciprocating pumping unit consisting of an elasticated convoluted diaphragm in the form of a bellows 15 located within housing 11.

Figure 2:
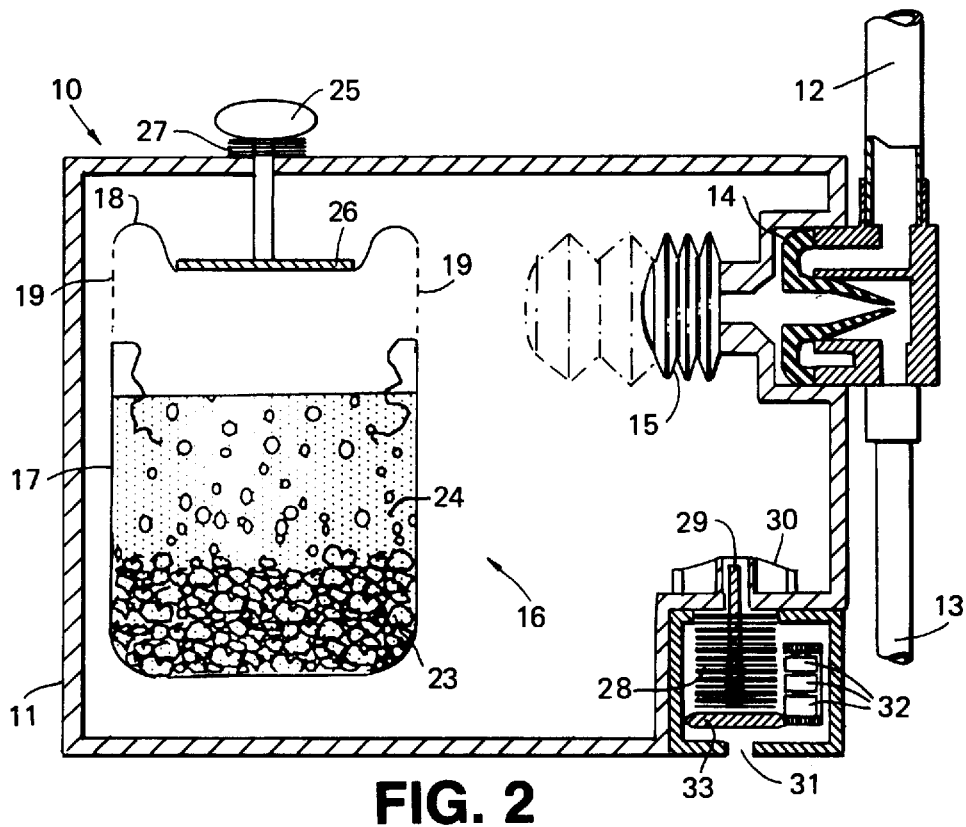
FIG. 2 is an end elevation of the device of FIG. 1, in use.

Bellows 15 is shown in a relaxed (extended) state in FIG. 1, but it can also be elastically compressed to pump liquid therefrom through valve 14 and out of delivery tube 13 as shown in FIG. 2. A subsequent relaxation of bellows 15 causes liquid to be drawn thereinto from supply tube 12 via valve 14. Thus, a reciprocating movement of bellows 15 will cause the pulsatile pumping of liquid from the nutritive liquid supply to the patient.

Compression of the bellows 15 is effected by the generation of gas in housing 11 by gas generating means indicated generally at 16. Gas generating means 16 comprises a container 17 having a resilient flexible top section 18 and gas permeable, liquid impermeable wall sections 19. A frangible membrane 20 divides the interior of container 17 into a dry upper chamber 21 and a reservoir 22 situated below the membrane.

Upper chamber 21 is filled with chips of sodium bicarbonate 23 and reservoir 22 contains citric acid solution 24. A plunger 25 operable from the exterior of housing 11 is used to actuate gas generating means 16. When plunger 25 is depressed it causes a plate 26 to depress flexible top section 18 of housing 17, thereby exerting pressure on upper chamber 21. This pressure breaks frangible membrane 20 (as illustrated in FIG. 2) and the sodium bicarbonate chips 23 drop into the citric acid solution 24 thereby generating carbon dioxide gas which escapes from container 17 via gas permeable wall sections 19. The resultant pressurisation of the interior of housing 11 compresses bellows 15 from its extended state (shown in dotted outline in FIG. 2) to a compressed state as illustrated in FIG. 2.

In FIG. 2, plunger 25 is shown depressed, but in reality plunger 25 is depressed and then released, at which point a spring 27 causes plunger 25 to return to the position shown in FIG. 1.

Figure 3:
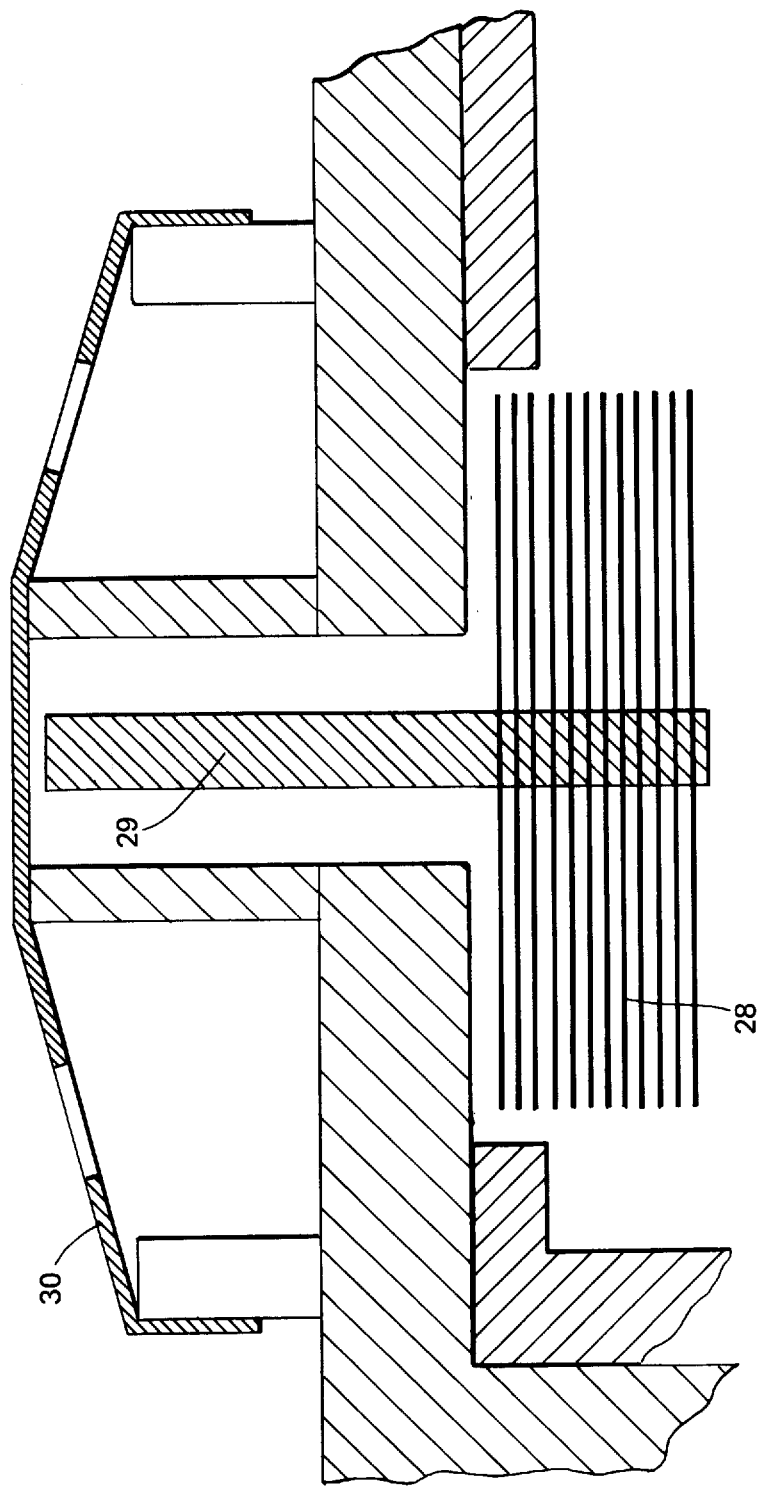
FIG. 3 is an end elevation in section of a variation on the device of FIG. 1.

After a predetermined amount of time has elapsed (sufficient at least to ensure that bellows 15 has been properly compressed), the interior of housing 11 is decompressed using a venting mechanism illustrated in more detail in FIG. 3. An electromagnet 28 is actuated causing a rod 29 to move upwards thereby lifting an elastic venting membrane 30 to allow gas to escape from the interior of housing 11 via an aperture 31.

When the interior of housing 11 equalises with atmospheric pressure, bellows 15 (which was elastically compressed) returns to its relaxed (extended) state. Electromagnet 28 remains energised for a sufficient length of time to ensure that bellows 15 relaxes completely. As long as electromagnet 28 is energised, the interior of housing 11 will remain at atmospheric pressure (despite the fact that gas is being generated by gas generating means 16), and one can always thus ensure that bellows 15 re-extends completely. After a predetermined period of time electromagnet 28 is de-energised, rod 29 drops to the position illustrated and membrane 30 again seals the interior of housing 11 from the atmosphere, at which point the continued generation of gas repressurizes housing 11, thereby starting the cycle again.

It will be appreciated that valve 14 allows liquid to move in one direction only. When bellows 15 is being compressed by the increasing pressure within housing 11, valve 14 prevents liquid from being pushed backed into supply tube 12 and causes it to be ejected instead through delivery tube 13. Conversely, when housing 11 is depressurized and bellows 15 elastically re-extends to its relaxed position, valve 14 causes liquid to be drawn into bellows 15 from supply tube 12 and prevents it from being drawn back through delivery tube 13.

Thus, the continued reciprocation of valve 14 gives rise to a two-stroke pumping cycle: in each cycle a fixed volume of liquid (equal to the difference in volumes between the extended bellows and compressed bellows) is drawn from supply tube 12 and pumped through delivery tube 13. It is necessary to ensure that the pressure within housing 11 is allowed to build up to a sufficient level and for a sufficient length of time to give rise to a predetermined compression of bellows 15, irrespective of variations in the viscosity of the liquid being pumped. Similarly, it is necessary to ensure that the interior of housing 11 is allowed to depressurize to a sufficient extent and for a sufficient length of time to ensure that bellows 15 re-extends completely, irrespective of variations in the viscosity of the liquid being pumped. If a viscous liquid is being pumped it will be appreciated that while the interior of housing 11 depressurizes almost instantaneously, the state of depressurization must be maintained for a sufficient length of time to allow bellows 15 to slowly draw the viscous liquid from supply tube 12 as it re-extends itself from the elastically compressed state.

The pumping cycle is therefore controlled by the venting mechanism which comprises electromagnet 28, rod 29 and membrane 30. The energization of electromagnet 28 is powered by batteries 32 in conjunction with an electromagnetic controller 33 (which comprises a simple clock circuit controlling an on-off switch). Controller 33 can be programmable to allow liquid to be pumped at different rates or it can be fixed (for a one-rate delivery of a particular liquid).

By ensuring that the venting mechanism remains closed and opened for sufficient lengths of time as indicated above, one can always ensure that a complete bellows volume is pumped during each two-stroke cycle irrespective of variations in the viscosity of the liquid being pumped. This gives rise to a precise pumping rate in contrast to the viscosity-dependent rates known from the prior art. It will also be appreciated that the mechanism illustrated is extremely simple and cheap to construct.

Figure 4:
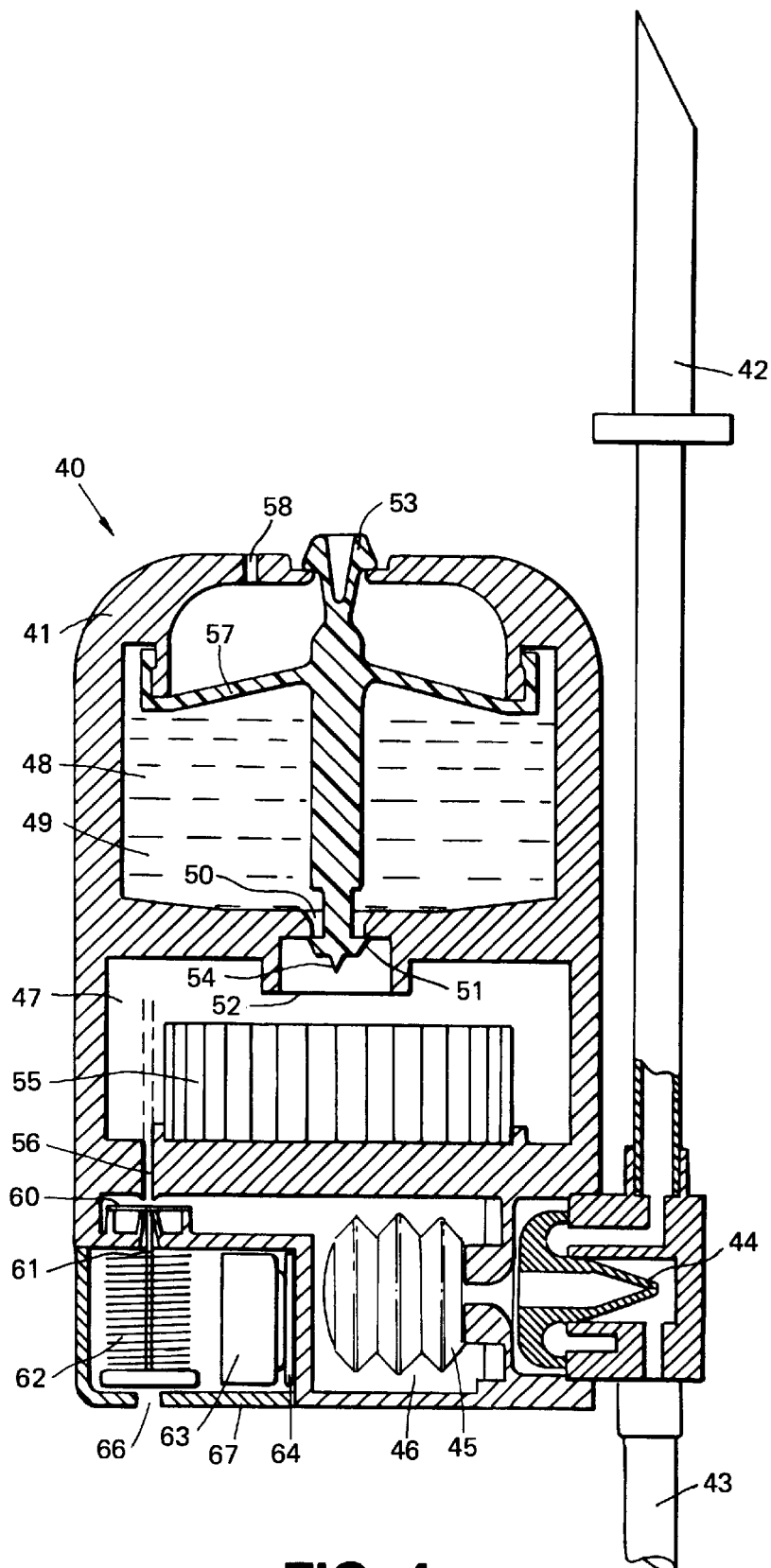
FIG. 4 is an end elevation in section of a second embodiment of a liquid delivery device according to the invention.

Referring now to FIG. 4, there is indicated, generally at 40 a second and more sophisticated embodiment of the invention. Device 40 comprises a housing 41 which receives a supply tube 42, which leads for example from a nutritive liquid supply (not shown), and a delivery tube 43 which leads to a patient. A nutritive liquid can therefore pass from the nutritive liquid supply to the patient via an inlet/outlet valve 44 which permits communication between the tubes 42,43 via a reciprocating pumping unit consisting of an elasticated convoluted diaphragm in the form of a bellows 45 located in a pumping chamber 46.

Valve 44 and bellows 45 cooperate to draw liquid from supply tube 42 and pump it through delivery tube 43 as described above with reference to the device of FIGS. 1–3. There are differences, however, in the method of pressurising and depressurizing pumping chamber 46.

Compression of the bellows 45 is effected by the generation of gas in a gas generation chamber 47. Gas generation chamber 47 is located below a reservoir 48 containing a citric acid solution 49. The reservoir 48 is provided with an aperture 50 which is sealed by a rubber seal 51 before use. A layer of aluminium foil 52 ensures a completely sterile seal. In use, a trigger 53 is depressed thereby pushing seal 51 downwards and causing a needle 54 to penetrate the foil layer 52. Thus, communication between reservoir 48 and gas generation chamber 47 is effected. It will be appreciated that the arrangement of the trigger 53 and the seal 51 is such that the distance moved by the seal 51 in use is minimal.

A sodium bicarbonate tablet 55 is located in the gas generation chamber 47 directly under aperture 50, such that the citric acid solution 49 drips onto the sodium bicarbonate tablet 55 when the trigger 53 is depressed. An immediate and spontaneous chemical reaction occurs resulting in the generation of carbon dioxide and an increase of pressure in the gas generation chamber 47. The gas is transmitted to pumping chamber 46 by means of a conduit 56 which extends (shown in dotted outline in FIG. 4) into the gas generation chamber 47 and which provides a means of communication between the pumping chamber 46 and the gas generation chamber 47. Alternatively, the conduit 56 can comprise an aperture provided with a hydrophobic filter.

As citric acid 49 drips steadily onto the sodium bicarbonate 55, gas generation is continued and the pressure in pumping chamber 46 rises, causing the contraction of bellows 45 and the pumping of liquid contained therein through valve 44 and out of the delivery tube 43. When the bellows 45 is fully contracted, the rising pressure within the pumping chamber 46 and the gas generation chamber 47 exerts an upwards pressure on a membrane 57 which is connected to seal 51, thereby causing seal 51 to rise and block aperture 50. This upward movement of the membrane 57 is facilitated by exhausting of air through a vent 58. It will be appreciated that the degree of elasticity of the membrane can be selected so as to exercise a degree of control on the gas generating reaction. The gas generating reaction is therefore cut off by the increasing pressure within housing 41 after bellows 45 is empty. Under certain conditions the pressure required to cause the aperture 50 to be blocked could be reached prior to the complete emptying of the bellows 45. However, this will not affect the operation of the pumping mechanism. As pumping chamber 46 and gas generation chamber 47 form a sealed enclosure, the increased pressure is maintained indefinitely, thereby keeping aperture 50 sealed. In order to complete the pumping cycle (i.e. allowing bellows 45 to relax and draw in liquid from supply tube 42 in preparation for the next cycle), pumping chamber 46 is provided with means for releasing the pressure.

Figure 5:
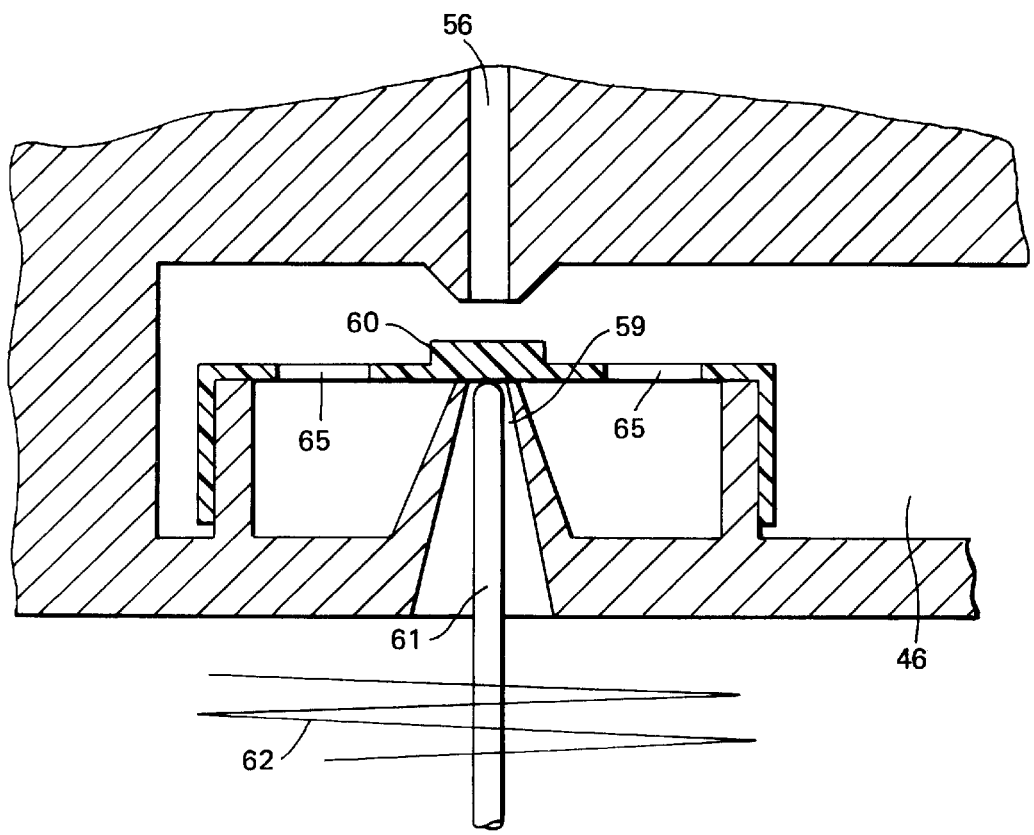
FIG. 5 is an end elevation in section illustrating a detail of the device of FIG. 4.

The means for releasing the pressure is similar to that illustrated in FIG. 3, and can be better understood by referring additionally to FIG. 5, where it can be seen that the chamber 46 is provided with an aperture 59 sealed by a flexible membrane 60. A rod 61 extends from an electromagnet 62 to a point immediately below the membrane 60. The electromagnet 62 is connected to a battery 63 and electronic controller 64. When energised, the electromagnet 62 causes the rod 61 to rise, pushing the membrane 60 upwards thereby unblocking the aperture 59 and simultaneously blocking the conduit 56. Gas can therefore escape from the chamber 46 through the aperture 59 via holes 65 provided in the membrane 60. The aperture 59 is in communication with the environment via an opening 66 (see FIG. 4). Thus, the pressure in pumping chamber 46 is free to equalise with atmospheric pressure when the electromagnet 62 is energised. The consequent reduction in pressure in the pumping chamber 46 allows the elastic bellows 45 to relax, refilling as it does so by drawing liquid from the supply tube 42.

The length of time during which the electromagnet 62 is energised is determined by electronic controller 64 to ensure that the bellows 45 is completely filled with liquid before the next cycle begins. A high viscosity liquid may require the equalisation step to continue for a relatively long period of time, and some nutritive liquids may have a variable viscosity causing uncertainty in predicting the length of time required for the bellows 45 to relax and refill. The controller 64 can be linked to a sensor which detects the complete expansion of the bellows 45 and maintains the electromagnet 52 in an energised state until complete expansion has been detected.

It will be appreciated that throughout this period of time, the gas generation chamber 47 remains sealed and pressurised and therefore the aperture 50 also remains sealed. This greatly economises on the citric acid 49 and sodium bicarbonate 55 used, as no gas is being generated until it is actually necessary. This inert state can be maintained for as long a period as is required (this will be determined by the desired pumping rate). When the electromagnet 62 is de-energised, the rod 61 drops back to the position illustrated in FIGS. 4 and 5, thereby re-establishing communication between the pumping chamber 46 and the gas generation chamber 47, and simultaneously resealing the aperture 59. The pressure equalises between the two chambers, and the consequent drop in pressure in the pumping chamber 47 allows the membrane 57 to relax somewhat, thereby permitting seal 51 to drop, unblocking the aperture 50 and causing the recommencement of the gas generation reaction as the citric acid 49 again begins to drip onto the sodium bicarbonate tablet 55.

Accordingly, using this embodiment, a pumping cycle can be established which provides a suitable controlled rate of liquid delivery. The controller 64 determines this pumping cycle, and an extra element of control is provided by the feedback mechanism which cuts off the chemical reaction when it is not needed (i.e. when the bellows 45 is fully compressed).

The pumping cycle is also determined in part by the relative volumes of the pumping chamber 46 and the gas generation chamber 47. When the membrane 60 relaxes to equalise the pressures between the two chambers, the chamber 47 is at an elevated pressure and the chamber 46 is at atmospheric pressure.

If the pumping chamber 46 is large relative to the gas generation chamber 47, then the pressure within the pumping chamber 46 will only rise minimally, while the pressure within the gas generation chamber 47 will fall back almost to atmospheric pressure. If, on the other hand, the gas generation chamber 47 is large relative to the pumping chamber 46, the pumping chamber 46 will be repressurized to a much greater extent and the gas generation chamber 47 will only depressurize slightly, causing the bellows 45 to be compressed much more quickly.

Thus, the designer can create a pumping profile by varying such factors as the relative sizes of the chambers 46,47, the relative size and elasticity of the bellows 45, the size of the conduit 56 and of the aperture 59, to name just a few of the parameters determining the delivery rate.

Figure 6:
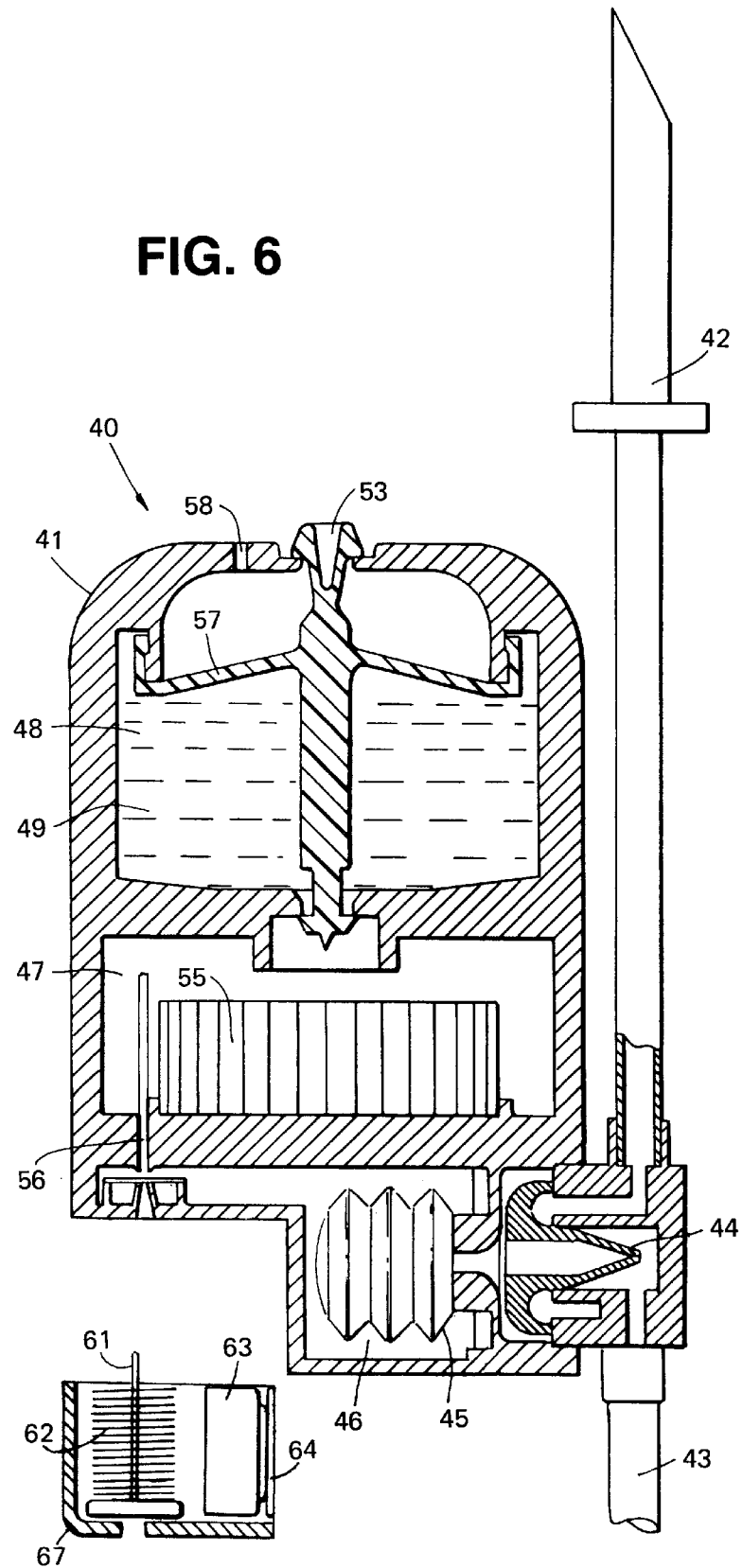
FIG. 6 is an end elevation in section of a variation on the device of FIG. 4.
Figure 7:
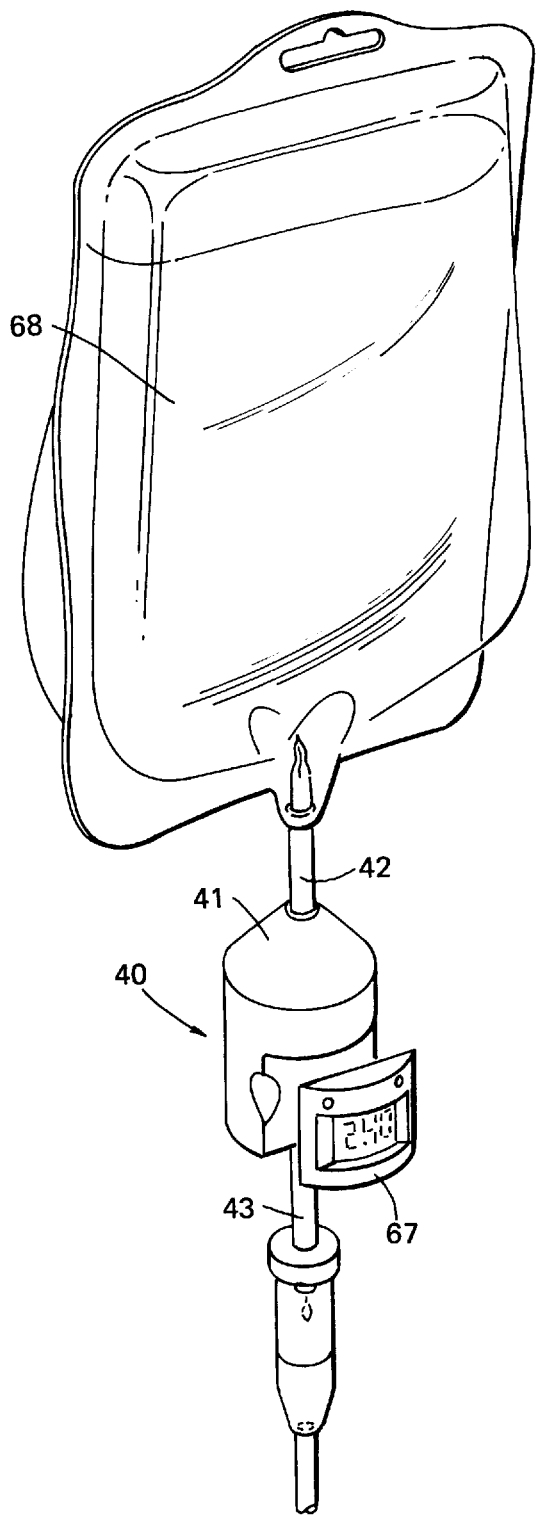
FIG. 7 is a perspective view of a liquid delivery device according to the invention.

FIG. 6 illustrates the device 40 in two sections, showing that rod 61, electromagnet 62, battery 63 and controller 64 are provided as part of an electronic control unit 67 which is separable from the housing 41. It is envisaged that the control unit 67 would be reusable, while the housing 41 would be disposable after a single use (although this does not necessarily have to be the case).

The views illustrated in FIGS. 4–6 are schematic representations of the components of device 40. FIGS. 7–10 provide perspective views of actual embodiments of a liquid delivery pumping device according to the invention. Thus, it can be seen that the device 40 comprises a housing 41 intermediate a supply tube 42 communicating with a nutritive liquid reservoir 68 and a delivery tube 43. Housing 41 constitutes a disposable portion of the device, as indicated above, and it detachably receives an electronic control unit 67 which is used to control the rate at which liquid is pumped from the reservoir 68 to the patient.

Figure 8:
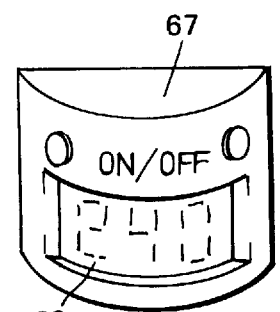
FIGS. 8–10 are perspective views of variations on an electronic control unit forming part of the device of FIG. 4.
Figure 9:
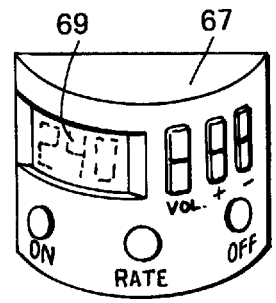
Figure 10:
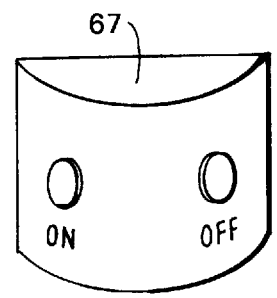

FIGS. 8, 9 and 10 illustrate different embodiments of electronic control unit 67. Thus, the embodiment in FIG. 8 is a relatively simple embodiment having a preprogrammed cycle and providing a visual display 69 of the volume of liquid pumped. FIG. 9 illustrates a sophisticated embodiment which can be programmed by the user or by medical staff to adjust the rate and total volume of liquid pumped, while also providing a visual display 69.

Finally, FIG. 10 illustrates a very simple embodiment of electronic control unit 67, which is preprogrammed and does not provide any visual display, being provided only with on/off functions.

Figure 11:
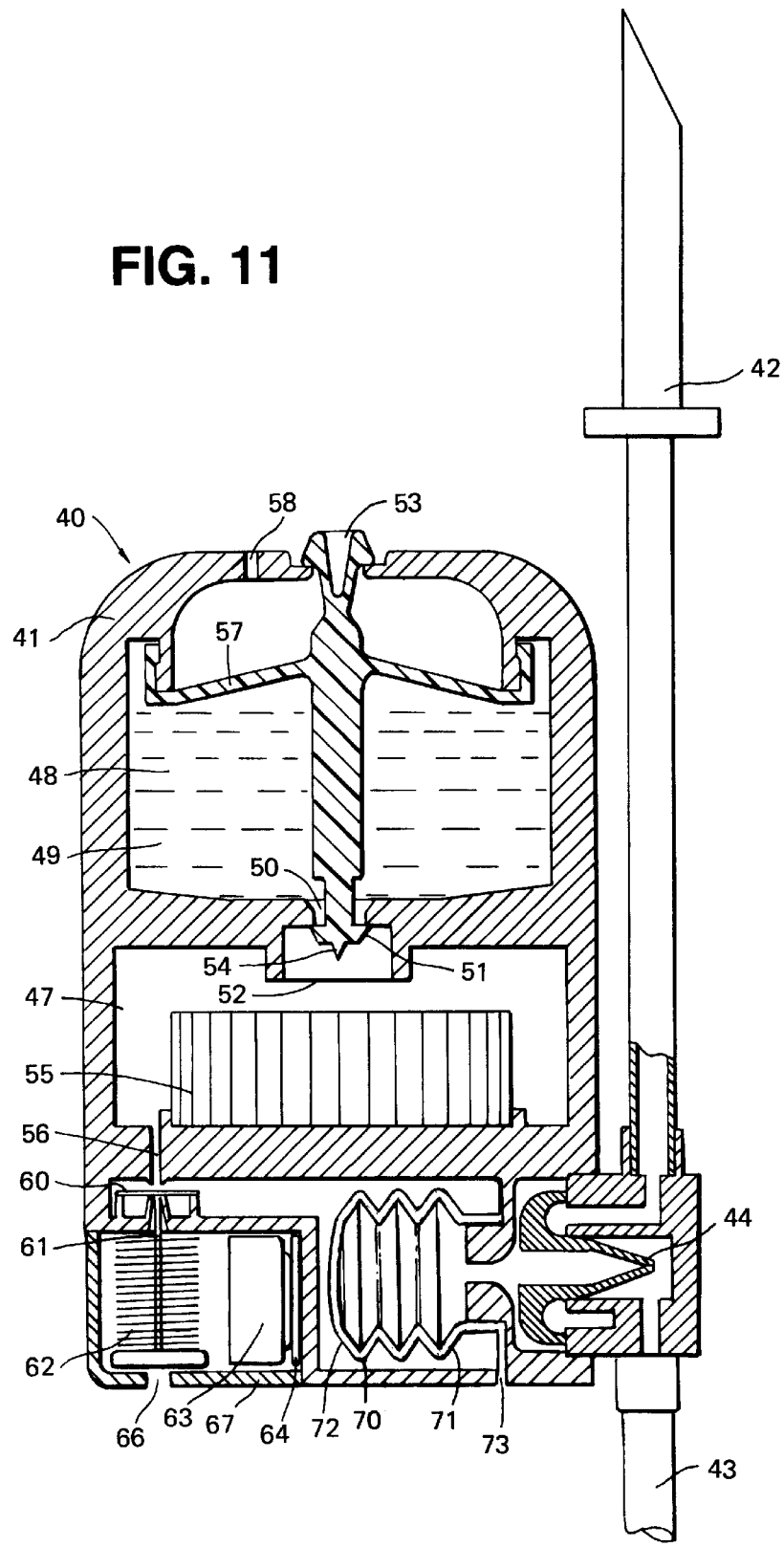
FIG. 11 is an end elevation in section of a third embodiment of a liquid delivery device according to the invention.

Referring to FIG. 11, there is illustrated a variant on the embodiment of FIG. 4 and wherein like parts are denoted by like numerals. Accordingly, it will be noted that the device 40 of FIG. 11 differs from the device 40 of FIG. 4 in that the bellows has an inner wall 70 and an outer wall 71 defining a channel 72 therebetween through which gas can escape to atmosphere through a vent 73 if the outer wall 71 of the bellows is perforated. This type of device is especially suitable when the liquid to be delivered is intended for parenteral administration rather than enteral administration.

Figure 12:
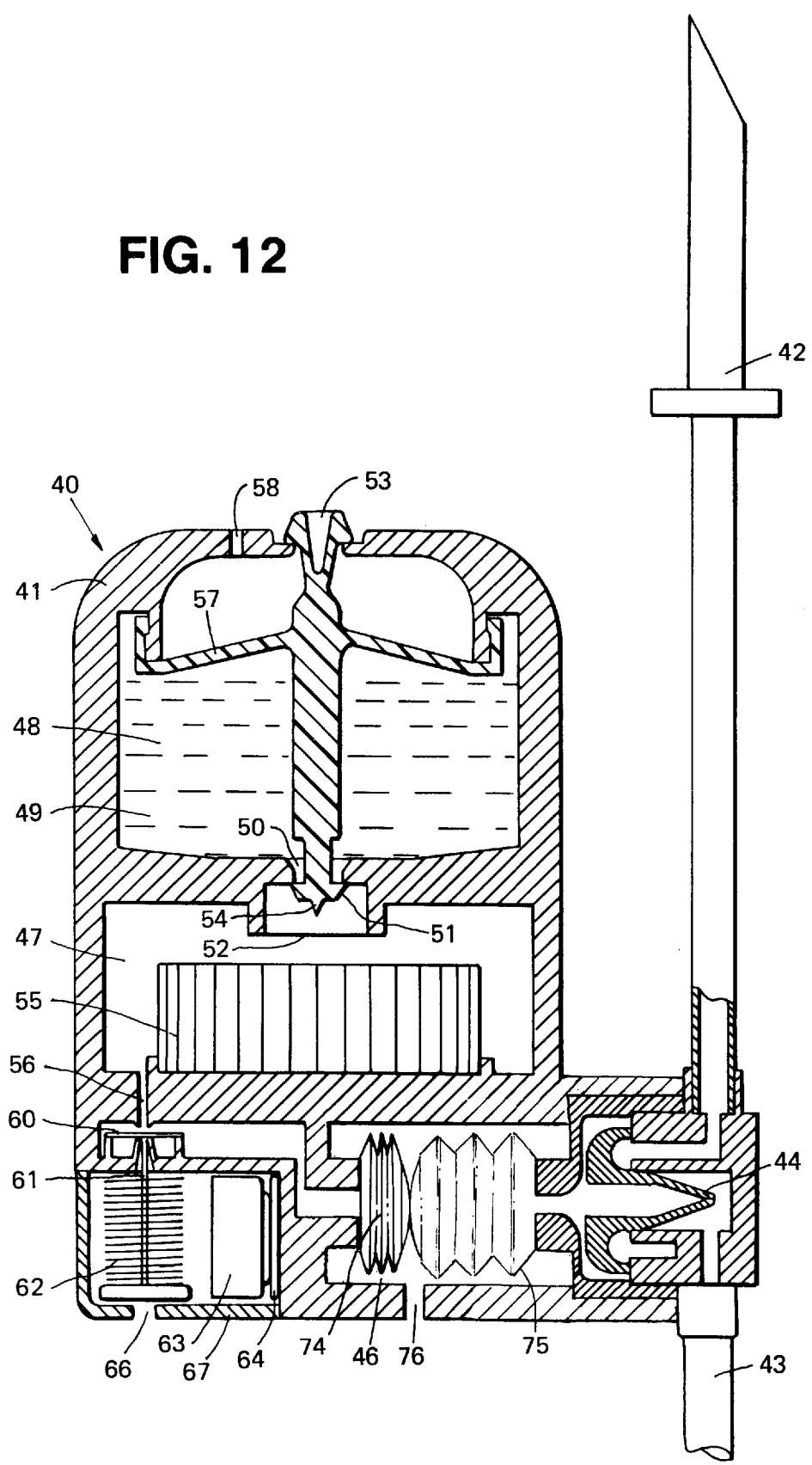
FIG. 12 is an end elevation in section of a fourth embodiment of a liquid delivery device according to the invention.

The device of FIG. 12 is a further variant on the device of FIG. 4 and again like parts are denoted by like numerals. In this embodiment the bellows 45 of FIG. 4 is replaced by a pair of cooperating bellows 74 and 75. The bellows 74 (shown in the compressed state) is operated on by the gas fed thereto via the conduit 56 in the manner of operation of the bellows 45 of FIG. 4. The reciprocating movement of the bellows 74 is transmitted to the bellows 75 which alternately compresses and relaxes in response to the movement of the bellows 74. Any gas escaping through the wall of the bellows 74 will vent to the atmosphere through the vent 76. This safety feature renders this embodiment particularly suitable for use in the administration of liquids via the parenteral route.

Figure 13:
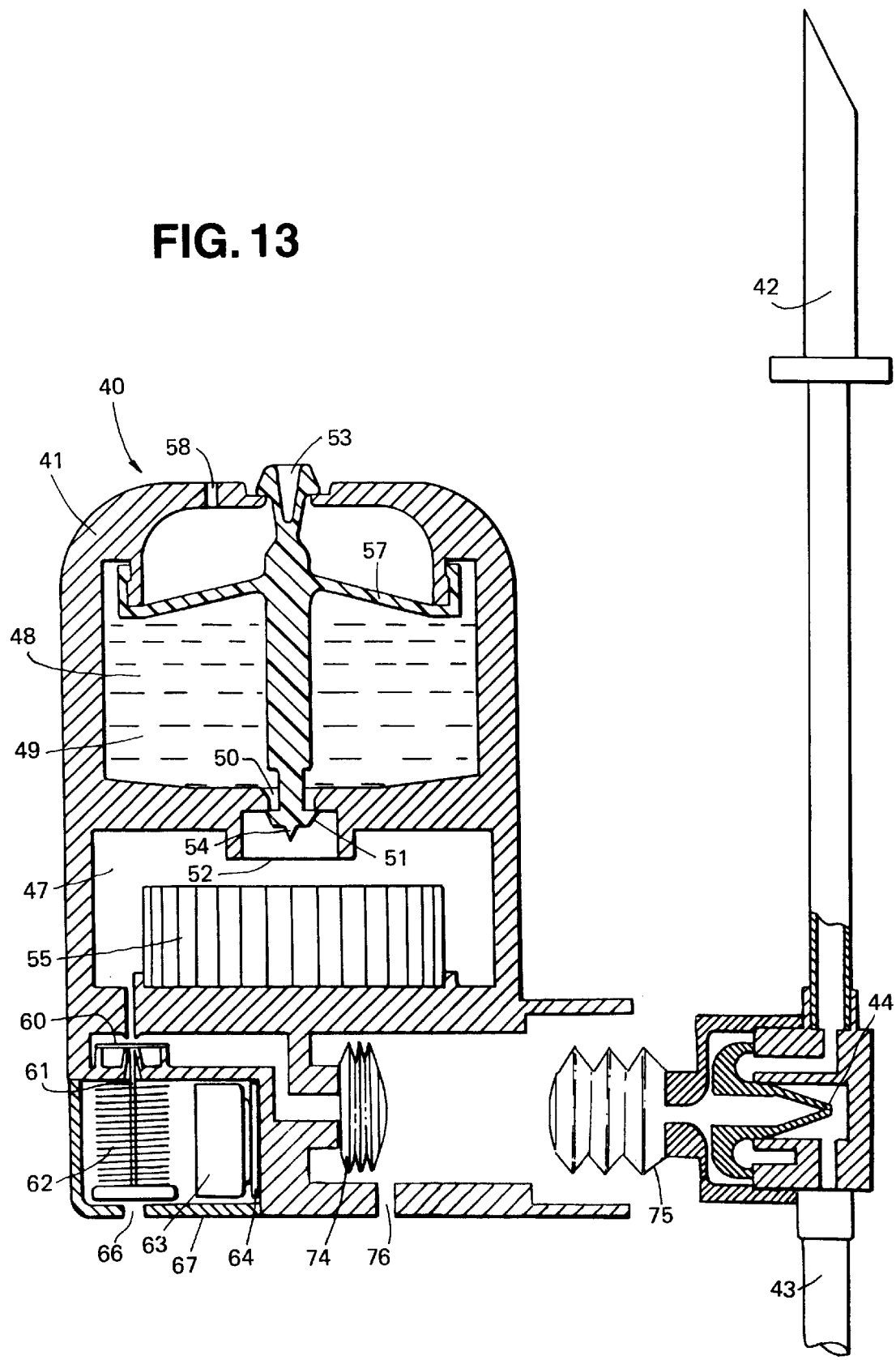
FIG. 13 is an exploded view of the device of FIG. 12.

As shown in greater detail in FIG. 13, the bellows 75 forms a unit with the valve 44 which is detachable from the device 40 for reuse once the gas generating reactants are exhausted.

Figure 14:
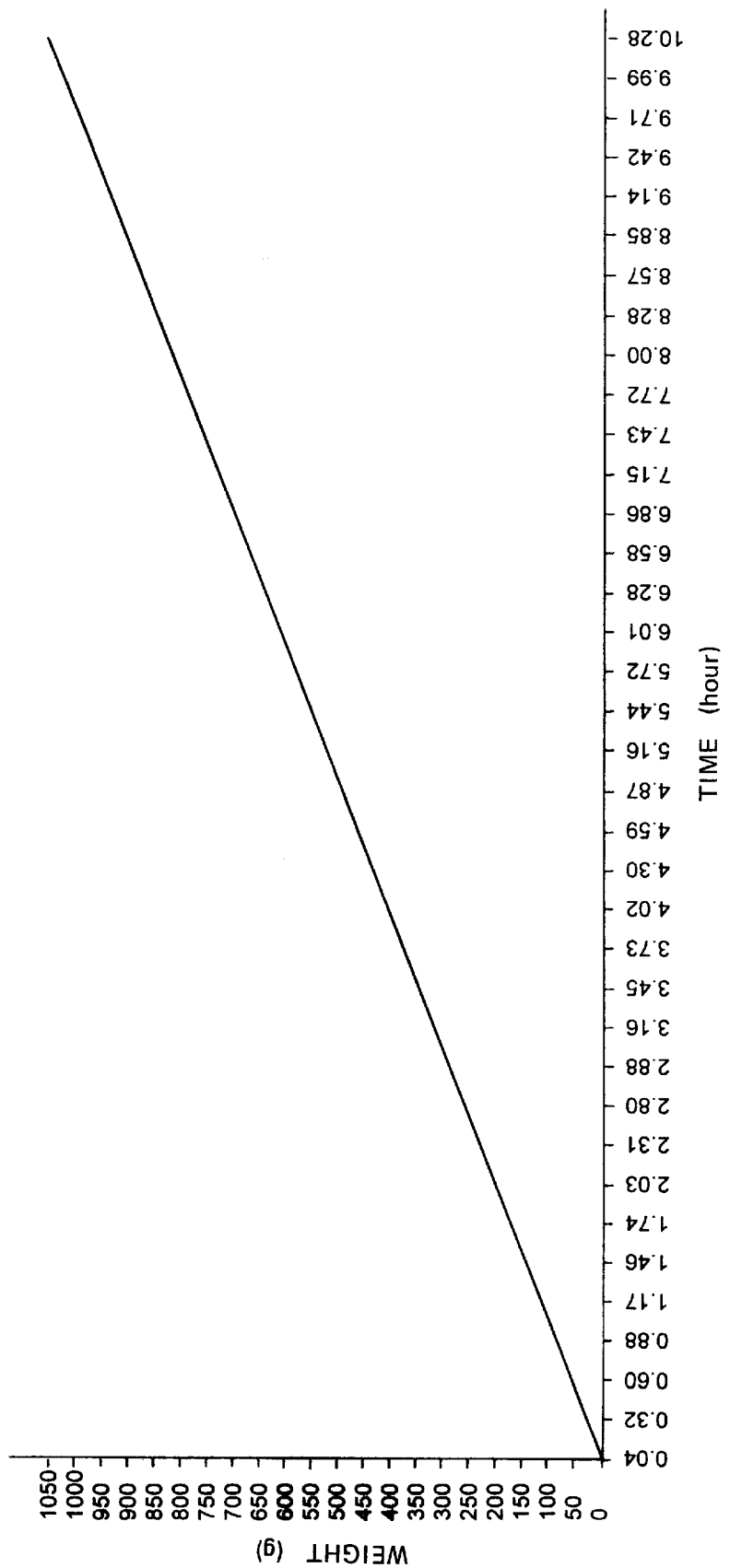
FIG. 14 is a graph showing the delivery rate (weight (g) versus time (hours)) using a device according to the invention.

FIG. 14 is a graph which shows the delivery rate of a liquid delivery pumping device according to the invention when such a device was used to pump the isotonic preparation for enteral nutrition sold by Ross Laboratories under the Trade Mark "OSMOLITE"; the average pumping rate obtained was 100.1 g/hour.

It can be seen from the near-perfect linearity of the graph that the delivery rate of the device is entirely constant over more than a ten hour period and the skilled person will appreciate that this constancy of delivery rate arises from the specific configuration of components used. If, for example, the electronic controller is set to ensure a complete contraction and refilling of the bellows (irrespective of liquid viscosity) every three minutes and the bellows volume is equivalent to the volume of 5 g liquid, then it can be seen that 100 g of liquid will be delivered per hour, even if there are fluctuations in viscosity with changes in temperature or fluctuations in viscosity arising from irregularities in the formulation of the liquid.

Thus, a controller can be designed or programmed to effect a particular delivery rate for any one of a number of liquid formulations of different viscosities simply by ensuring that the bellows is completely evacuated and refilled a set number of times per minute or hour. This alone guarantees a constant delivery rate and is independent of the viscosity of the liquid being delivered (although more strongly elastic bellows or wider orifices, valves and tubes may be required if it is envisaged that particularly viscous liquids will be delivered).

What is claimed is:

1. A liquid delivery device comprising a housing, a pumping chamber within the housing, gas generating means comprising reactants which when brought into contact generate a gas which pressurizes said pumping chamber, a pumping mechanism having a pumping member within the pumping chamber, said member being reciprocable in response to changes in pumping chamber pressure, wherein the reciprocation of the pumping member causes a liquid to be drawn from a liquid supply and pumped towards an outlet, and means for controlling the pressure within the pumping chamber to enable controlled reciprocation of the pumping member.

2. A device according to claim 1, wherein the means for controlling the pressure within the pumping chamber comprises a vent having associated control means.

3. A device according to claim 2, wherein the vent is an electronically controlled valve unit which when actuated releases gas from said pumping chamber.

4. A device according to claim 2, wherein the vent comprises an electromagnetically actuated valve member for selectively causing a venting aperture in the housing to be blocked and unblocked.

5. A device according to claim 1, wherein the pumping mechanism comprises valve means for causing liquid to be drawn from the liquid supply into the pumping mechanism and subsequently pumped from the pumping mechanism towards the outlet upon the reciprocation of the pumping member through a cycle.

6. A device according to claim 1, wherein the pumping member is in the form of a convoluted diaphragm.

7. A device according to claim 6, wherein the diaphragm is in the form of a bellows.

8. A device according to claim 7, wherein the bellows has inner and outer walls defining a channel therebetween through which gas can escape to atmosphere if the outer wall of the bellows is perforated.

9. A device according to claim 7, wherein the bellows comprises an elastic member which when relaxed causes the bellows to be extended but which can be elastically deformed allowing the bellows to be compressed under an increased chamber pressure.

10. A device according to claim 7, wherein liquid is drawn into the bellows and pumped therefrom during a cycle of reciprocation of the bellows, such that the volume of liquid which is pumped during each cycle of reciprocation is equal to the difference between the extended and compressed bellows volumes.

11. A device according to claim 7, wherein the means for controlling the pressure causes the pumping chamber pressure to vary cyclically, the cycle comprising a compression phase during which the pumping chamber is pressurized by the generation of gas to a sufficient pressure and for a sufficient time to cause the bellows to be compressed to a predetermined extent, and a relaxation phase during which the pumping chamber is depressurized by a sufficient amount and for a sufficient length of time to allow the bellows to re-extend to a draw in mined degree and thereby draw in a fixed volume of liquid to be pumped during the following cycle.

12. A device according to claim 7, wherein the pumping member is a first bellows and the pumping mechanism includes a second bellows cooperating with the first bellows such that the first bellows is operated on by said gas to cause reciprocation of the second bellows.

13. A device according to claim 12, wherein the pumping mechanism and the second bellows form a unit which is detachable from the device for reuse once the gas generating reactants are exhausted.

14. A device according to claim 12, wherein any gas escaping through the first bellows vents to the atmosphere.

15. A device according to claim 1, wherein the gas generating means comprises first and second compartments, each containing a reactant, said compartments being interconnected in a manner which permits the flow, in use, of a reactant from the first compartment to contact the other reactant.

16. A device according to claim 1, wherein the reactants are two reactants which consist of the components of an effervescent couple.

17. A device according to claim 16, wherein the reactants are citric acid and either sodium bicarbonate or sodium carbonate and the gas generated is carbon dioxide.

18. A device according to claim 1, wherein at least one rupturable seal separates said reactants prior to the reaction of and generation of gas thereby.

19. A device according to claim 1, further comprising a gas generation chamber in which said gas is generated and which is in communication with said pumping chamber.

20. A device according to claim 19, further comprising blocking means for preventing further ingress of gas into the pumping chamber while gas is being released therefrom.

21. A device according to claim 20 wherein said blocking means is incorporated into said pressure controlling means.

22. A device according to claim 21, wherein said blocking means comprises a blocking member which is controllably movable from a first position, in which it blocks a venting aperture between the pumping chamber and the atmosphere, to a second position in which it blocks communication between the gas generation chamber and the pumping chamber, such that the movement of the blocking member between the first and second positions enables the pumping chamber to be selectively pressurized and depressurized.

23. A device according to claim 19, wherein an increase in pressure within the gas generation chamber prevents continued mixing of the reactants.

24. A device according to claim 23, wherein one of said reactants is in liquid form and flows from a compartment into contact with at least one of the other of said reactants and wherein an increase in pressure within the gas generation chamber reduces the rate of flow of said one of said reactants.

25. A device according to claim 24, wherein the pumping member is in the form of a convoluted diaphragm.

26. A device according to claim 1, wherein the gas generating means enables a gas to be generated intermittently.

* * * * *